United States Patent
Pikkula et al.

(10) Patent No.: US 10,143,635 B2
(45) Date of Patent: Dec. 4, 2018

(54) ARTIFICIAL SALIVA

(71) Applicant: Forward Science Technologies, LLC, Stafford, TX (US)

(72) Inventors: Brian Pikkula, Sugar Land, TX (US); Robert J. Whitman, West University Place, TX (US)

(73) Assignee: Forward Science Technologies, LLC, Stafford, TX (US)

( * ) Notice: Subject to any disclaimer, the term of this patent is extended or adjusted under 35 U.S.C. 154(b) by 0 days.

(21) Appl. No.: 15/424,100

(22) Filed: Feb. 3, 2017

(65) Prior Publication Data

US 2017/0216169 A1     Aug. 3, 2017

Related U.S. Application Data

(60) Provisional application No. 62/290,772, filed on Feb. 3, 2016.

(51) Int. Cl.

| | | |
|---|---|---|
| A61K 45/06 | (2006.01) |
| A61K 9/14 | (2006.01) |
| A61K 8/24 | (2006.01) |
| A61K 33/42 | (2006.01) |
| A61K 9/00 | (2006.01) |
| A61K 9/08 | (2006.01) |
| A61K 33/00 | (2006.01) |
| A61K 33/14 | (2006.01) |
| A61K 33/06 | (2006.01) |
| A61Q 11/00 | (2006.01) |
| A61K 8/20 | (2006.01) |
| A61K 8/19 | (2006.01) |
| A61K 8/02 | (2006.01) |
| A61K 47/02 | (2006.01) |

(52) U.S. Cl.
CPC ............ *A61K 8/24* (2013.01); *A61K 8/0204* (2013.01); *A61K 8/19* (2013.01); *A61K 8/20* (2013.01); *A61K 9/006* (2013.01); *A61K 9/0063* (2013.01); *A61K 9/08* (2013.01); *A61K 33/00* (2013.01); *A61K 33/06* (2013.01); *A61K 33/14* (2013.01); *A61K 33/42* (2013.01); *A61K 45/06* (2013.01); *A61K 47/02* (2013.01); *A61Q 11/00* (2013.01); *A61K 2800/5922* (2013.01)

(58) Field of Classification Search
CPC ...... A61K 2300/00; A61K 45/06; A61K 9/14; A61K 9/0095
See application file for complete search history.

(56) References Cited

U.S. PATENT DOCUMENTS

| | | | | |
|---|---|---|---|---|
| 6,306,372 B1 * | 10/2001 | Stier | ......................... | A61K 8/27 424/49 |
| 2006/0182811 A1 * | 8/2006 | Edwards | ................ | A61K 35/16 424/531 |
| 2011/0086108 A1 * | 4/2011 | Weldon | ................. | A61K 31/167 424/602 |
| 2014/0294990 A1 * | 10/2014 | O'Connor | .............. | A61K 33/14 424/641 |
| 2014/0314827 A1 * | 10/2014 | Melman | ............... | A61K 31/155 424/442 |
| 2015/0030694 A1 * | 1/2015 | Kobus | .................... | A61K 33/00 424/606 |
| 2016/0175356 A1 * | 6/2016 | Weldon | .................. | A61K 9/006 424/602 |

OTHER PUBLICATIONS

Facts and Comparisons® eAnswers—website, URL—online. factsandcomparisons.com/MonoDisp.aspx?monoID=fandc-hcp14030&quick=880285%7c5&search=880285%7c5&isstemmed=True&NDCmapping=-1&fromTop=true#firstMatch, accessed on Jul. 13, 2015, Clinical Drug Information, LLC, 1 pg.

* cited by examiner

*Primary Examiner* — Tracy Liu
(74) *Attorney, Agent, or Firm* — Boisbrun Hofman, PLLC

(57) ABSTRACT

A composition for mixing with water for use as an oral rinse, comprising monobasic sodium phosphate, dibasic sodium phosphate, sodium chloride, and calcium chloride.

2 Claims, No Drawings

ARTIFICIAL SALIVA

CROSS-REFERENCE TO RELATED APPLICATIONS

This application claims priority to and the benefit of U.S. Provisional Application No. 62/290,772, titled "Artificial Saliva," filed Feb. 3, 2016, the entire disclosure of which is hereby incorporated herein by reference.

BACKGROUND OF THE DISCLOSURE

There are many artificial saliva products intended for human consumption in treating various ails of the human oral cavity. However, such salivary preparations are far from fully satisfactory.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting.

The present disclosure introduces an artificial saliva that is provided in disposable packets. The artificial saliva is comprised of powdered ingredients that, when combined with a predetermined amount (e.g., 30 mL or 1 oz.) of water, produces a supersaturated calcium phosphate solution. The artificial saliva may be packaged in single-use packets. The artificial saliva may be provided non-sterile, and perhaps not intended to be sterilized before use.

The artificial saliva may be administered several times per day. Thus, the artificial saliva may primarily be used at home, office, or other non-clinical settings. However, the artificial saliva may also be used in clinical or healthcare facility settings where patients are receiving inpatient services.

The artificial saliva relieves chronic and temporary xerostomia and mucositis. The artificial saliva is a partial substitute for natural saliva, and is effective to moisten, lubricate, and clean the oral cavity, including the mucosa of the mouth, tongue, and throat. Thus, the artificial saliva may facilitate chewing and speaking, and may also relieve bad breath.

The artificial saliva may be used to treat dryness of the mouth or throat (e.g., hyposalivation, xerostomia, mucositis), regardless of the cause, and regardless of whether the condition is temporary or permanent. The artificial saliva relieves dryness of the oral mucosa and/or ameliorates pain.

The artificial saliva may also be used as an adjunct to standard oral care in treating the mucositis that may be caused by radiation or high dose chemotherapy.

The artificial saliva may also be used for the relief of dryness of the oral mucosa when hyposalivation results from surgery, radiotherapy, chemotherapy, infection or dysfunction of the salivary glands, inflammation of the mouth or throat, fever, emotional factors such as fear or anxiety, obstruction of the salivary ducts, Bell's Palsy, and Sjogren's syndrome. The artificial saliva may also be used for dryness of the oral mucosa occurring from using various drugs, such as antihistamines, atropine, or other anticholinergeic agents that suppress salivary secretion.

The artificial saliva may be used as part of an oral hygiene program for patients with dry mouth. The artificial saliva provides intensive hygiene of the oral cavity, and may be used to help relieve bad taste, relieve offensive nasal discharge, and crusting.

Each use may comprise orally rinsing with the artificial saliva for one minute (or some other predetermined time period) and then expectorating, and perhaps repeating. Thus, the artificial saliva is considered a surface-contacting device with a limited duration of contact. The artificial saliva may be used up to a maximum rinse time of 20 minutes per day (e.g., 2 minutes per application x maximum 10 times per day).

The artificial saliva is formulated as a supersaturated solution of calcium and phosphate ions. The artificial saliva is composed of monobasic and dibasic sodium phosphate, sodium bicarbonate, sodium chloride, and calcium chloride, each of which are USP grade (U.S. Pharmacopeial Convention). The artificial saliva may also include silicon dioxide, which is FCC grade (USP Food Chemicals Codex). The artificial saliva has an in-solution pH range of 6.25-7.5 (e.g., about 6.69), and is soluble in water.

The artificial saliva is packaged as a powder in a sealed packet for mixing with water just prior to use. The amount of powder in the sealed packet may be just sufficient for a single use, which may include two rinsing cycles, such as about 351 mg of the powder.

In the powdered form, the individual components and their respective weight percent may be as in Table 1 below.

TABLE 1

| Ingredient | Weight Percent |
| --- | --- |
| Sodium phosphate, monobasic | 2.8 |
| Sodium phosphate, dibasic | 2.8 |
| Sodium bicarbonate | 4.6 |
| Sodium chloride | 72.6 |
| Calcium chloride | 14.2 |

In another embodiment form, the individual components and their respective weight percent may be as in Table 2 below.

TABLE 2

| Ingredient | Weight Percent |
| --- | --- |
| Sodium phosphate, monobasic | 2.7 |
| Sodium phosphate, dibasic | 2.7 |
| Sodium bicarbonate | 4.3 |
| Sodium chloride | 68.9 |
| Calcium chloride | 18.6 |
| Silicon dioxide | 2.7 |

However, embodiments other than those in Tables 1 and 2 are also within the scope of the present disclosure, including those in Tables 3 and 4 below.

TABLE 3

| Ingredient | Weight Percent |
| --- | --- |
| Sodium phosphate, monobasic | 0.5-5.0 |
| Sodium phosphate, dibasic | 0.5-5.0 |

TABLE 3-continued

| Ingredient | Weight Percent |
| --- | --- |
| Sodium bicarbonate | 1.0-10.0 |
| Sodium chloride | 55.0-87.5 |
| Calcium chloride | 10.0-30.0 |

TABLE 4

| Ingredient | Weight Percent |
| --- | --- |
| Sodium phosphate, monobasic | 0.5-5.0 |
| Sodium phosphate, dibasic | 0.5-5.0 |
| Sodium bicarbonate | 1.0-10.0 |
| Sodium chloride | 55.0-87.5 |
| Calcium chloride | 10.0-30.0 |
| Silicon dioxide | 0.5-5.0 |

Additional components may be added to the rinse to reduce inflammation, and/or to act as an analgesic/analgesic, antimicrobial, and/or antifungal agent.

In view of the entirety of the present disclosure, including the claims, a person having ordinary skill in the art will readily recognize that the present disclosure introduces a composition comprising an oral care mixture for use in a human oral cavity, the oral care mixture comprising: monobasic sodium phosphate; dibasic sodium phosphate; sodium bicarbonate; sodium chloride; and calcium chloride.

The oral care mixture may comprise, by weight: between about 0.5% and about 5.0% of monobasic sodium phosphate; between about 0.5% and about 5.0% dibasic sodium phosphate; between about 1.0% and about 10.0% of sodium bicarbonate; between about 55.0% and about 87.5% of sodium chloride; and between about 10.0% and about 30.0% of calcium chloride.

The oral care mixture may comprise, by weight: about 2.8% monobasic sodium phosphate; about 2.8% dibasic sodium phosphate; about 4.6% sodium bicarbonate; about 72.6% sodium chloride; and about 14.2% calcium chloride.

The oral care mixture may further comprise silicon dioxide. For example, the oral care mixture may comprise, by weight: between about 0.5% and about 5.0% of monobasic sodium phosphate; between about 0.5% and about 5.0% dibasic sodium phosphate; between about 1.0% and about 10.0% of sodium bicarbonate; between about 55.0% and about 87.5% of sodium chloride; between about 10.0% and about 30.0% of calcium chloride; and between about 0.5% and about 5.0% silicon dioxide. In another example, the oral care mixture may comprise, by weight: about 2.7% monobasic sodium phosphate; about 2.7% dibasic sodium phosphate; about 4.3% sodium bicarbonate; about 68.9% sodium chloride; about 18.6% calcium chloride; and about 2.7% silicon dioxide.

The oral care mixture may further comprise at least one of an anti-inflammatory, an analgesic and/or anesthetic, an antimicrobial, and an antifungal. The anti-inflammatory may be or comprise one or more of diclofenac, felbinac, ketoprofen, and piroxicam. The analgesic and/or anesthetic may be or comprise one or more of capsaicin, eugenol, guaiacol, lidocaine, benzocaine, acemannan, oil of cinnamon, and oil of clove. The antimicrobial may be or comprise one or more of xylitol, calcium alginate, chitosan, iodoform, and chlorobutanol. The antifungal may be or comprise one or more of chlorobutanol, nystatin, clotrimazole, and amphotericin B.

The oral care mixture may be for dissolving in water to form an oral rinse solution.

The composition may further comprise water, and the composition may be an oral rinse solution.

The composition may relieve symptoms of dryness of the oral cavity.

The present disclosure also introduces a composition consisting of an oral care mixture for use in a human oral cavity, the oral care mixture consisting of: monobasic sodium phosphate; dibasic sodium phosphate; sodium bicarbonate; sodium chloride; and calcium chloride.

The oral care mixture may consist of, by weight: between about 0.5% and about 5.0% of monobasic sodium phosphate; between about 0.5% and about 5.0% dibasic sodium phosphate; between about 1.0% and about 10.0% of sodium bicarbonate; between about 55.0% and about 87.5% of sodium chloride; and between about 10.0% and about 30.0% of calcium chloride.

The oral care mixture may consist of, by weight: about 2.8% monobasic sodium phosphate; about 2.8% dibasic sodium phosphate; about 4.6% sodium bicarbonate; about 72.6% sodium chloride; and about 14.2% calcium chloride.

The present disclosure also introduces a composition comprising an oral care mixture for use in a human oral cavity, the oral care mixture comprising: monobasic sodium phosphate; dibasic sodium phosphate; sodium chloride; and calcium chloride.

The oral care mixture may further comprise silicon dioxide.

The oral care mixture may further comprise at least one of an anti-inflammatory, an analgesic and/or anesthetic, an antimicrobial, and an antifungal. The anti-inflammatory may be or comprise one or more of diclofenac, felbinac, ketoprofen, and piroxicam. The analgesic and/or anesthetic may be or comprise one or more of capsaicin, eugenol, guaiacol, lidocaine, benzocaine, acemannan, oil of cinnamon, and oil of clove. The antimicrobial may be or comprise one or more of xylitol, calcium alginate, chitosan, iodoform, and chlorobutanol. The antifungal may be or comprise one or more of chlorobutanol, nystatin, clotrimazole, and amphotericin B.

The oral care mixture may be for dissolving in water to form an oral rinse solution.

The composition may further comprise water, and the composition may be an oral rinse solution.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. § 1.72(b) to permit the reader to quickly ascertain the nature of the technical disclosure. It is submitted with the understanding that it will not be used to interpret or limit the scope or meaning of the claims.

What is claimed is:

1. A composition consisting of, by weight:
about 2.8% monobasic sodium phosphate;
about 2.8% dibasic sodium phosphate;
about 4.6% sodium bicarbonate;
about 72.6% sodium chloride; and
about 14.2% calcium chloride.

2. A composition consisting of, by weight:
about 2.7% monobasic sodium phosphate;
about 2.7% dibasic sodium phosphate;
about 4.3% sodium bicarbonate;
about 68.9% sodium chloride;
about 18.6% calcium chloride; and
about 2.7% silicon dioxide.

* * * * *